US00PP18083P2

(12) United States Plant Patent

Hofmann et al.

(10) Patent No.: US PP18,083 P2

(45) Date of Patent: Sep. 25, 2007

(54) *EUPHORBIA* PLANT NAMED 'INNTHAL'

(50) Latin Name: *Euphorbia amygdaloides×Euphorbia characias ssp. wulfenii*
Varietal Denomination: Innthal

(75) Inventors: Silvia Hofmann, Mainz (DE); Susanne Herdegen, Dexheim (DE)

(73) Assignee: InnovaPlant GmbH + Co. KG, Gensingen (DE)

( * ) Notice: Subject to any disclaimer, the term of this patent is extended or adjusted under 35 U.S.C. 154(b) by 0 days.

(21) Appl. No.: 11/236,746

(22) Filed: Sep. 27, 2005

(51) Int. Cl.
*A01H 5/00* (2006.01)

(52) U.S. Cl. ..... Plt./302

(58) Field of Classification Search ..... Plt./302
See application file for complete search history.

(56) References Cited

PUBLICATIONS

UPOV CR–ROM Plant Variety Database 2006/01. Search for cultivar Innthal.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Euphorbia* plant named 'Innthal', characterized by its compact and mounded plant habit; freely branching habit; early flowering habit; large dark green-colored flower bracts; and good garden performance.

1 Drawing Sheet

Botanical designation: *Euphorbia amygdaloides×Euphorbia characias* ssp.*wulfenii.*
Cultivar denomination: 'Innthal'.

BACKGROUND OF THE INVENTION

The present Invention relates to a new and distinct cultivar of *Euphorbia* plant, botanically known as *Euphorbia amygdaloides×Euphorbia characias* ssp. *wulfenii,* and hereinafter referred to by the cultivar name Innthal.

The new *Euphorbia* is a product of a planned breeding program conducted by the Inventors in Gensingen, Germany. The objective of the breeding program is to create new compact *Euphorbia* plants with attractive foliage and flower coloration.

The new *Euphorbia* originated from a cross-pollination made by the Inventors in the spring of 1998 of the *Euphorbia amygdaloides* cultivar Purpurea, not patented, as the female, or seed parent, with an unnamed selection of *Euphorbia characias* ssp. *wulfenii,* not patented, as the male, or pollen parent. The new *Euphorbia* was discovered and selected as a single plant from within the resulting progeny of the cross-pollination in a controlled environment in Gensingen, Germany in the spring of 1999.

Asexual reproduction of the new cultivar by terminal vegetative cuttings since May, 1999 in Gensingen, Germany has shown that the unique features of this new *Euphorbia* are stable and reproduced true to type in successive generations.

SUMMARY OF THE INVENTION

Plants of the cultivar Innthal have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Innthal'. These characteristics in combination distinguish 'Innthal' as a new and distinct cultivar:

1. Compact and mounded plant habit.
2. Freely branching habit.
3. Early flowering habit.
4. Large dark green-colored flower bracts.
5. Good garden performance.

In side-by-side comparisons conducted in Gensingen, Germany, plants of the new *Euphorbia* differed from plants of the female parent, the cultivar Purpurea in the following characteristics:

1. Plants of the new *Euphorbia* were more compact than plants of the cultivar Purpurea.
2. Plants of the new *Euphorbia* were more freely branching than plants of the cultivar Purpurea.
3. Plants of the new *Euphorbia* had green-colored foliage whereas plants of the cultivar Purpurea had burgundy-colored foliage.
4. Plants of the new *Euphorbia* flowered earlier than plants of the cultivar Purpurea.
5. Plants of the new *Euphorbia* had rounded inflorescences whereas plants of the cultivar Purpurea had elongated inflorescences.

In side-by-side comparisons conducted in Gensingen, Germany, plants of the new *Euphorbia* differed from plants of the male parent selection in the following characteristics:

1. Plants of the new *Euphorbia* were more compact than plants of the male parent selection.
2. Plants of the new *Euphorbia* and the male parent selection differed in flower bract coloration.
3. Plants of the new *Euphorbia* had rounded inflorescences whereas plants of the male parent selection had cylindrical inflorescences.

Plants of the new *Euphorbia* can be compared to plants of the *Euphorbia* cultivar Imprefant, disclosed in U.S. Plant patent application Ser. No. 11/113,385. In side-by-side comparisons conducted in Gensingen, Germany, plants of the new *Euphorbia* differed from plants of the cultivar Imprefant in the following characteristics:

1. Plants of the new *Euphorbia* had green-colored leaves whereas plants of the cultivar Imprefant had burgundy-colored leaves.
2. Plants of the new *Euphorbia* were more freely flowering than plants of the cultivar Imprefant.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Euphorbia*.

The photograph at the top of the sheet is a close-up view of typical flowers of 'Inneuphhel'.

The photograph at that bottom of the sheet comprises a side perspective view of a typical plant of 'Inneuphhel' grown in a container.

DETAILED BOTANICAL DESCRIPTION

The aforementioned photographs and following observations and measurements describe plants grown in Bonsall, Calif., in an outdoor nursery during the spring and summer under full sun conditions with day temperatures ranging from 10° C. to 32° C. and night temperatures ranging from 2° to 21° C. After planting rooted cuttings, plants were grown for about 22 weeks with one plant per 12.5-cm container. Plants were pinched one time. Color references are made to The Royal Horticultural Society Colour Chart, 1995 Edition, except where general terms of ordinary dictionary significance are used.

Botanical classification: *Euphorbia amygdaloides*× *Euphorbia characias* ssp.*wulfenii* cultivar Innthal.

Parentage:

*Female parent.*—*Euphorbia amygdaloides* cultivar Purpurea, not patented.

*Male parent.*—Unnamed selection of *Euphorbia characias*ssp. *wulfenii,* not patented.

Propagation:

*Type.*—By cuttings.

*Time to initiate roots, summer.*—About 14 days at 20° C.

*Time to initiate roots, winter.*—About 18 days at 20° C.

*Time to develop roots.*—About 20 days at temperatures of 20° C.

*Root description.*—Fine, white in color.

*Rooting habit.*—Freely branching.

Plant description:

*Plant form and growth habit.*—Compact and mounded plant habit; upright to somewhat outwardly spreading; inverted triangle; perennial subshrub. Moderate growth rate.

*Branching habit.*—Freely branching, usually about ten lateral branches develop per plant; dense and bushy plant form.

*Plant height.*—About 30 cm.

*Plant diameter.*—About 40 cm.

*Lateral branch description.*—Length: About 26 cm. Diameter: About 5 mm. Internode length: About 6 mm. Strength: Strong. Texture: Pubescent. Color: 145A.

Foliage description:

*Arrangement.*—Alternate to whorled; simple.

*Length.*—About 6.3 cm.

*Width.*—About 1.4 cm.

*Shape.*—Elliptical.

*Apex.*—Acute.

*Base.*—Attenuate.

*Margin.*—Entire.

*Texture, upper and lower surfaces.*—Pubescent.

*Venation.*—Pinnate, arcuate.

*Color.*—Developing foliage, upper surface: 147A. Developing foliage, lower surface: 147B. Fully developed foliage, upper surface: 147A. Mature foliage, lower surface: More gray than 147B. Venation, upper surface: 145B. Venation, lower surface: 146D.

*Petiole.*—Length: About 4 mm. Diameter: About 2 mm. Texture, upper and lower surfaces: Pubescent. Color, upper and lower surfaces: 144A.

Inflorescence description:

*Natural flowering season.*—Spring to summer in Southern California; flowering continuous during this period.

*Flower arrangement.*—Single rotate flowers arranged in umbel-like compound terminal cymes. Freely flowering with about 120 flower buds and flowers per plant. Flowers face upright and outwardly. Flowers persistent. Flowers not fragrant.

*Inflorescence height.*—About 14 cm.

*Inflorescence diameter.*—About 6 cm.

*Flower diameter.*—About 5 mm.

*Flower depth* (*height*).—About 7 mm.

*Flower longevity on the plant.*—About ten days.

*Floral bracts.*—Quantity/arrangement: Two; opposite. Length: About 1.25 to 1.5 cm. Width: About 2.5 cm. Shape: Orbicular. Apex: Rounded and emarginate. Base: Fused. Margin: Entire. Texture, upper and lower surfaces: Glabrous; smooth. Color: When opening and fully expanded, upper surface: 147A. When opening and fully opened, lower surface: 147B.

*Peduncles.*—Length: About 7.3 cm. Diameter: About 2 mm. Strength: Strong. Angle: Erect to about 45° from vertical. Texture: Smooth, glabrous. Color: 146B.

*Cyathia.*—Length: About 7 mm. Diameter: About 5 mm. Shape: Oval; eight terminal points; sessile. Aspect: Upright. Color: 145A.

*Nectaries.*—Quantity per flower: About four. Shape: Lunate. Length: About 2 mm. Width: About 3 mm. Color: 145A.

*Reproductive organs.*—Androecium: Quantity: About three to four stamens per cyathia. Shape: Oval, bi-lobed. Length: Less than 1 mm. Color: 145C. Pollen: Scarce. Pollen color: 12A. Gynoecium: Quantity: One per cyathia. Pistil length: About 6 mm. Style length: About 1 mm. Style color: 145D. Stigma shape: Six-parted. Stigma color: 144B. Ovary color: 145D.

*Fruit/seed.*—Fruit and seed production has not been observed.

Disease/pest resistance: Plants of the new *Euphorbia* not been observed to be resistant to pests and pathogens common to *Euphorbia*.

Temperature tolerance: Plants of the new *Euphorbia* are tolerant to temperatures as low as −6° C. and as high as 40° C.

It is claimed:

1. A new and distinct *Euphorbia* plant named 'Innthal', as illustrated and described.

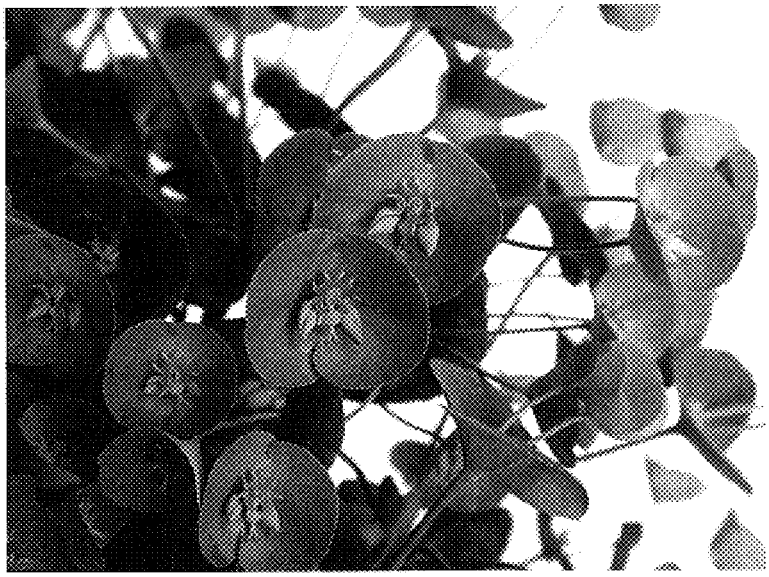
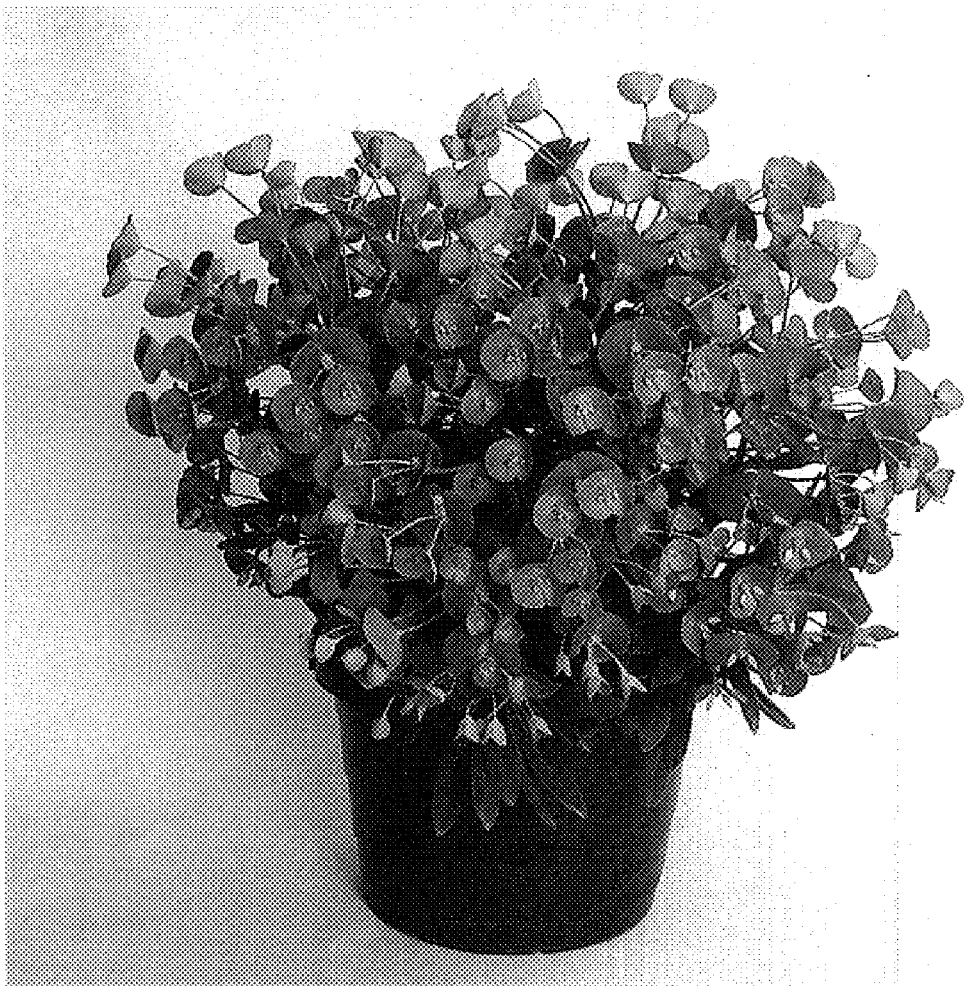

* * * * *